(12) United States Patent
Hutchison et al.

(10) Patent No.: US 10,839,949 B1
(45) Date of Patent: Nov. 17, 2020

(54) SYSTEMS AND METHODS FOR CONTROLLING DATA WORKFLOW

(71) Applicant: Express Scripts Strategic Development, Inc., St. Louis, MO (US)

(72) Inventors: David Hutchison, Collinsville, IL (US); Corinne Bradley-Pollack, Hillsboro, MO (US); Kevin Mulligan, Minneapolis, MN (US); Leah Sterman-Kabrt, West Caldwell, NJ (US); Melissa Orlando, Saint Ann, MO (US); Laurie Littlecreek, Foristell, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 519 days.

(21) Appl. No.: 15/710,793

(22) Filed: Sep. 20, 2017

Related U.S. Application Data

(60) Provisional application No. 62/397,522, filed on Sep. 21, 2016.

(51) Int. Cl.

| | | |
|---|---|---|
| *G06Q 10/00* | (2012.01) | |
| *G16H 10/60* | (2018.01) | |
| *G06Q 10/10* | (2012.01) | |
| *G06F 19/00* | (2018.01) | |

(52) U.S. Cl.
CPC ........... *G16H 10/60* (2018.01); *G06F 19/326* (2013.01); *G06F 19/3481* (2013.01); *G06Q 10/10* (2013.01)

(58) Field of Classification Search
CPC .... G06F 21/10; G06F 21/6209; G06F 19/325; G06F 21/6245; G06F 19/328; G06F 19/3418; G06F 19/3481; G06F 19/3468; G06F 19/3456; G06F 19/321; G06Q 20/02; G06Q 20/12; G06Q 20/24; G06Q 50/24; G06Q 10/00; G16H 10/60; G16H 40/20; G16H 50/20; G16H 40/67; G16H 40/63; G16H 10/65; G16H 50/70; G16H 20/10
See application file for complete search history.

(56) References Cited

U.S. PATENT DOCUMENTS

| | | |
|---|---|---|
| 8,781,854 B1 | 7/2014 | Harris |
| 2011/0029445 A1* | 2/2011 | Whittacre .............. G06Q 10/06 705/317 |
| 2012/0173391 A1 | 7/2012 | Korhnak |
| 2013/0132106 A1 | 5/2013 | Perry |

(Continued)

*Primary Examiner* — Maroun P Kanaan
(74) *Attorney, Agent, or Firm* — Small Patent Law Group LLC

(57) ABSTRACT

A method includes receiving a data access request at a computing system. The data access request is for completion of a first data processing task using the computing system. The method also includes accessing a plurality of first document types associated with a plurality of data processing tasks that include the first data processing task. The plurality of first document types indicates which of various subsets of data are required to complete the plurality of data processing tasks. The method also includes accessing a plurality of second document types that indicate assignments of the plurality of data processing tasks to a plurality of system requestors that includes the first system requestor, and executing the first data processing task based on the plurality of first document types and the plurality of second document types.

20 Claims, 9 Drawing Sheets

(56) References Cited

U.S. PATENT DOCUMENTS

| | | |
|---|---|---|
| 2015/0220690 A1 | 8/2015 | Kahlon |
| 2015/0278469 A1 | 10/2015 | Kahlon |
| 2015/0371001 A1 | 12/2015 | Pinsonneault et al. |
| 2015/0371203 A1 | 12/2015 | Plunkett et al. |
| 2016/0042147 A1 | 2/2016 | Maurer et al. |
| 2016/0092642 A1 | 3/2016 | Maurer et al. |
| 2016/0103978 A1 | 4/2016 | Stong |

\* cited by examiner

| Work Request | ID | CD1 | CD2 | MD1 | MD2 | MD3 | PSD1 | PSD2 | Group | Priority | Completed |
|---|---|---|---|---|---|---|---|---|---|---|---|
| TOR A | 53224 | 1 | 0 | 1 | 1 | 1 | 1 | 1 | 395 | 2 | 0 |
| TOR B | 33152 | 1 | 1 | 1 | 0 | 1 | 0 | 0 | 395 | 1 | 1 |
| TOR C | 56411 | 1 | 1 | 0 | 1 | 1 | 1 | 1 | 486 | 0 | 1 |
| Report BC | 21135 | 1 | 1 | 0 | 1 | 0 | 0 | 1 | 395 | 3 | 0 |
| TOR D | 64632 | 1 | 1 | 1 | 0 | 0 | 0 | 0 | 939 | 0 | 0 |
| Report ABC | 96720 | 1 | 0 | 0 | 1 | 1 | 1 | 0 | 486 | 0 | 0 |
| TOR B | 63122 | 1 | 0 | 1 | 0 | 1 | 1 | 1 | 842 | 0 | 0 |

FIGURE 3

| Work Request | ID | CD1 | CD2 | CD3 | MD1 | MD2 | MD3 | PSD1 |
|---|---|---|---|---|---|---|---|---|
| TOR A (Live) | 53224 | 1 | 9/20/2016 | Humalog | Jane Doe | Type 1 diabetic | Company B | Company Address |
| TOR A (WIP) | 53224 | 1 | 9/20/2016 | Humalog | Jane Smith | Type 1 diabetic | Company A | Company Address |
| TOR B (Live) | 73960 | 1 | | Medication Z | John Smith | | Company A | Company Address |
| TOR B (WIP) | 73960 | 0 | | Medication Z | John Smith | | Company A | Company Address |

FIGURE 4

| TOR A | | | |
|---|---|---|---|
| Request ID: | 53224 | Member Name: | *Jane Smith* }– 702 |
| Member Eligibility: | Yes | Member Condition: | Type 1 diabetic }– 706 |
| Fill Date: | 9/20/16 | Sponsor: | *Company A* }– 704 |
| Medication: | Humalog | Company Address: | 123 Main St., Anytown, State US 12345 |

TOR B

| | | | |
|---|---|---|---|
| Request ID: | 73960 | Member Name: | John Smith — 806 |
| Member Eligibility: | *No* — 802 | Member Condition: | N/A |
| Fill Date: | N/A | Sponsor: | Company A |
| Medication: | Medication Z | Company Address: | 123 Main St., Anytown, State US 12345 |

SYSTEMS AND METHODS FOR CONTROLLING DATA WORKFLOW

CROSS-REFERENCE TO RELATED APPLICATIONS

This application claims priority to U.S. Provisional Application No. 62/397,522, which was filed on 21 Sep. 2016, and the entire disclosure of which is incorporated herein by reference.

FIELD

The present disclosure relates generally to the technical field of data processing. In a specific example, the present disclosure may relate to systems and methods for controlling data workflow, which may include establishing restrictions on which data is available to operators examining the data, summarizing the changes made to the data to simplify review of changes to the data, and/or linking data representative of requests for processing the data.

BACKGROUND

A large amount of information may be used to determine which pharmacies can process and fill the prescriptions and prescription orders, and how the prescriptions and prescription orders are processed and filled by the pharmacies. This information can be extensive and complex due to the vast amount of pharmacies and other providers, as well as the arrangements for which pharmacies and other providers are permitted to process and fill prescriptions and prescription orders for a large number of different purchasers having a large amount of different insurance plans.

Modifications to this information can have wide-ranging implications on the processing and filling of the prescriptions and prescription orders. Due to the large amount and complexity of the information, as well as the criteria on which pharmacies may process and fill prescriptions and prescription orders, erroneous changes to the information can pose a significant risk to the proper management and operation of the information, as well as to the ability of pharmacies and other providers to process and fill prescriptions and prescription orders. These erroneous changes may occur because an employee modifying some pharmaceutical data incorrectly changes other pharmaceutical data that is not relevant or is not needed to complete the task assigned to the employee, the employee changes the value(s) of the pharmaceutical data to incorrect values, and/or the sequence of multiple tasks involving changes to the pharmaceutical data are not completed in the correct order.

BRIEF SUMMARY

In one embodiment, a method includes receiving a data access request at a computing system. The data access request is for completion of a first data processing task using the computing system. The method also includes accessing a plurality of first document types associated with a plurality of data processing tasks that include the first data processing task. The plurality of first document types indicates which of various subsets of data are required to complete the plurality of data processing tasks. The method also includes accessing a plurality of second document types that indicate assignments of the plurality of data processing tasks to a plurality of system requestors that includes the first system requestor, and executing the first data processing task based on the plurality of first document types and the plurality of second document types.

In one embodiment, a tangible and non-transitory computer readable storage medium includes instructions that direct at least one processor to receive a data access request for completion of a first data processing task using a computing system, and access a plurality of first document types associated with a plurality of data processing tasks that include the first data processing task. The plurality of first document types indicates which of various subsets of data are required to complete the plurality of data processing tasks. The instructions also direct the at least one processor to access a plurality of second document types that indicate assignments of the plurality of data processing tasks to a plurality of system requestors that includes the first system requestor, and to execute the first data processing task based on the plurality of first document types and the plurality of second document types.

In one embodiment, a method includes receiving a data access request, at a computing system, for completion of a first data processing task using the computing system, and accessing a plurality of first document types associated with a plurality of data processing tasks that include the first data processing task. The plurality of first document types indicates which of various subsets of data are required to complete the plurality of data processing tasks. The method also includes accessing a plurality of second document types that indicate assignments of the plurality of data processing tasks to a plurality of system requestors that includes the first system requestor, accessing a plurality of third document types that indicate requirements for completion of a second data processing task prior to execution of the first data processing task, preventing execution of the first data processing task until execution of the second data processing task is completed, and executing the first data processing task based on the plurality of first document types and the plurality of second document types.

BRIEF DESCRIPTION OF THE DRAWINGS

The present disclosure will become more fully understood from the detailed description and the accompanying drawings.

FIG. 3 illustrates one example of a data structure representative of access data and/or work request data shown in FIG. 2 according to one example embodiment;

FIG. 4 illustrates one example of a data structure representative of the work request data shown in FIG. 2 according to one example embodiment;

FIG. 5 illustrates one example of a graphical user interface (GUI) presented on a display device by a benefit manager device according to one example embodiment;

FIG. 6 illustrates another example of a GUI presented on a display device by a benefit manager device according to one example embodiment;

In the drawings, reference numbers may be reused to identify similar and/or identical elements.

DETAILED DESCRIPTION

Figure 1:
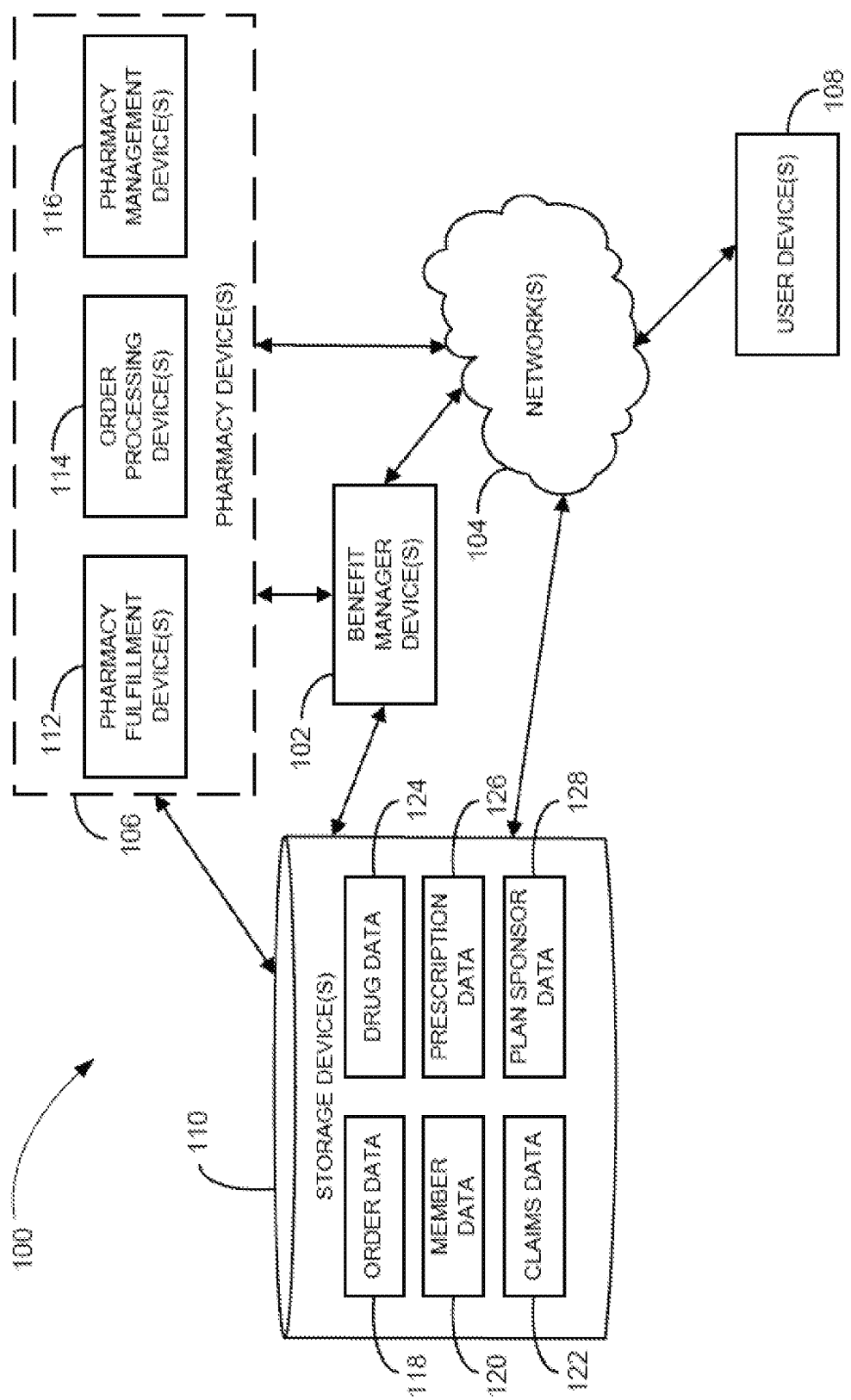
FIG. 1 is a diagram of an example implementation of a system for a high-volume pharmacy, according to an example embodiment.

Example systems and methods for controlling data workflow are described. In the following description, for purposes of explanation, numerous specific details are set forth in order to provide a thorough understanding of example embodiments. It will be evident, however, to one of ordinary skill in the art that these embodiments may be practiced without these specific details.

Creation or modification to data that relies on logic to determine which pharmacies can process and fill the prescriptions and prescription orders, and how the prescriptions and prescription orders are processed and filled by the pharmacies can have wide-ranging implications on the processing and filling of the prescriptions and prescription orders. Many known systems are maintained and updated by operators (also referred to as system requestors) changing portions of the pharmaceutical data used to determine which pharmacies can process and fill prescriptions and prescription orders, as well as how the pharmacies process and fill prescriptions and prescription orders. For example, as pharmacy benefits change, as members join or leave an insurance plan, as members change names or addresses, as new prescriptions are issued, as laws or regulations change in various parts of the country, etc., the information used to determine how to process and fill prescriptions and prescription orders may need to accordingly change.

In some embodiments, the systems and methods that control the workflow of modifications to pharmaceutical data by structuring memories used to store the pharmaceutical data so that operator access to the pharmaceutical data is restricted or limited to only the portions of the pharmaceutical data that is needed or associated with tasks assigned to the operator for completion. The operator may be able to complete tasks (also referred to as work requests, types of requests (TORs), or data processing tasks), using the data and/or logic for handling the data to which the operator has access. The work requests or types of requests may involve the operator changing which pharmacies or other providers can be used by a consumer having an insurance plan to process and fill prescriptions and prescription orders, changing details of the pharmacies or other providers (e.g., addresses and suspensions from insurance plans), adding pharmacies or other providers to insurance plans, or the like.

For example, the systems and methods can control the workflow of changes to the data responsive to receiving a data access request. The request can be to access data and complete a data processing task using the computing system, such as to change, add, or remove information from one or more subsets of the data described herein. The systems and methods access first document types associated with various data processing tasks to determine which subsets of data are needed to execute or otherwise complete the different tasks. Different tasks may require access to different portions (e.g., subsets) of the data in the computing system. The first document types (e.g., data structures such as tables, self-referential tables, databases, etc.) can indicate (e.g., list) which subsets of data are needed for completion of different tasks.

The systems and methods also access second document types that indicate assignments of the plurality of data processing tasks to a plurality of system requestors. These second document types (e.g., data structures such as tables, self-referential tables, databases, etc.) can indicate (e.g., list) which operators, users, etc. (system requestors) have been assigned different tasks to complete.

Using the information obtained from the first and second document types, the systems and methods can execute the data processing task (based on input from the system requestor, such as the changes to the data that are to be made). For example, the systems and methods can restrict which subsets of the data in the computing system are available to the system requestor to complete the task. This can help prevent the system requestor from intentionally or inadvertently changing data to which the requestor should not have access to (e.g., the data is confidential) and/or data that is not relevant or involved in the task assigned to the system requestor. The systems and methods can prevent the system requestor from performing another, different processing task due to the task not being assigned to the requestor and/or the data needed for the assigned task not being needed for the other task.

In some embodiments, the data representative of work requests assigned to one or more of the operators may be logically linked with each other. The data representative of these work requests may be linked by indicating a particular sequence or order that the work requests need to be completed within, by indicating that an error in a previously completed work request needs to be updated or fixed, or the like. The systems and methods may then prevent, restrict, or prohibit operators from performing the work requests in a manner that violates or contradicts the links between the data representative of the work requests.

For example, some data processing tasks may require that another processing task be completed first. The systems and methods can refer to third document types that indicate (e.g., list) prerequisites for completion of an assigned data processing task. For example, the task of changing the mailing address of a pharmacy may not be able to be completed until the task of adding the pharmacy to a network of pharmacies has been completed. The systems and methods can then prevent the system requestor from executing the assigned data processing task until the prerequisite data processing task is completed.

The portions of the data that are changed by system requestors may be identified and labeled as such for presentation to the operators and/or reviewers of the operators (for example, during quality review of the work of the operators). The labeling of the updated or changed data may assist the operators and/or reviewers in quickly and easily identifying which portions of the pharmaceutical data were changed or updated, the values to which these portions of the data were changed or updated, and whether these changes are correct or incorrect.

For example, the systems and methods can receive a data review request at the computing system from a reviewer, such as a system requestor that is reviewing the work of another system requestor for accuracy and/or completion. The systems and methods can access fourth document types that indicate a change to the subsets of the data due to execution of data processing tasks by system requestors. The systems and methods can create a fourth document type whenever a system requestor changes a subset of the data. The fourth document type can list or otherwise store the state of the portion of the data before the task was executed (the original or prior version of the data), the state of the portion of the data after the task was executed (the modified version of the data), and one or more other portions of the data that were not modified or otherwise left unchanged by execution of a data processing task. The reviewer can examine the fourth document type to determine if the task was accurately and completely executed. If so, the reviewer can save or otherwise approve the changes. In one embodiment, the reviewer enters or inputs a confirmation indicator in response to reviewing and approving the change to the data. This indicator can represent acceptance of the change to the data. Otherwise, the reviewer can reject the changes or correct the changes.

FIG. 1 is a block diagram of an example implementation of a system 100 for a pharmacy, according to an example embodiment. The system 100 is an example environment in which the methods and systems for controlling data workflow may be implemented. However, the methods and systems may be implemented in data processing environment that is not associated pharmacy technology. For example, the methods and systems may be used to control data workflow for a research system, a payroll system, a computer programming environment, an intelligence dissemination system, or the like.

While the system 100 is generally described as being deployed in a pharmacy or a fulfillment center (e.g., a mail order pharmacy, a direct delivery pharmacy, etc., and the like), the system 100 and/or components thereof may otherwise be deployed (e.g., in a lower volume pharmacy, etc.). A pharmacy may be a pharmacy that is capable of filling prescriptions automatically, mechanically, manually, or a combination thereof. The system 100 may include a benefit manager device 102, a pharmacy device 106, and a user device 108 in communicating with each other directly and/or over a network 104. The system may also include a data storage device 110.

The benefit manager device 102 is a device operated by an entity that is at least partially responsible for creation and/or management of the pharmacy or drug benefit. While such entity operating the benefit manager device 102 is typically a PBM, other entities may operate the benefit manager device 102 on behalf of themselves (i.e., the PBMs) or other entities. For example, the benefit manager device 102 may be operated by a health plan, a retail pharmacy chain, a drug wholesaler, a data analytics, or other type of software-related company, etc., or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long-term care benefit, a nursing home benefit, etc., and the like. The PBM may, in addition to its PBM operations, operate one or more than one pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store, etc.) from a pharmacist or a pharmacist technician. The member may also obtain the prescription drug through mail order drug delivery from a mail order pharmacy location, which may be the pharmacy system 100. In some embodiments, the member may obtain the prescription drug directly or indirectly through the use of a machine, such as a kiosk, vending unit, mobile electronic device, or a different type of mechanical, electrical, electronic communication device and/or computing device. Such a machine may be filled with the prescription drug in prescription packaging, which may include multiple prescription components, by the pharmacy system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, etc., or the like. In some instances, an employer of the member may directly or indirectly fund or reimburse the member for the copayments.

The amount of the copayment required by the member may vary with different pharmacy benefit plans having different plan sponsors or clients and/or for different prescription drugs. The member's copayment may be a flat copayment (e.g., $10, etc.), co-insurance (e.g., 10%, etc.), and/or a deductible (e.g., for first $500 of annual prescription drug expense, etc.) for certain prescription drugs, certain types and/or classes of prescription drugs, and/or all prescription drugs. The copayment may be stored in the data storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels used for the prescription drug to be received. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM, e.g., the benefit manager device, may perform certain adjudication operations including verifying eligibility for the member, identifying/reviewing an applicable formulary for the member to determine any appropriate copayment, coinsurance, and deductible for the prescription drug, and performing a drug utilization review (DUR) on the member. Further, the PBM may provide a response to the pharmacy, e.g., the pharmacy system 100, following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances, these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on types of pharmacy network in which the pharmacy is included. In some embodiments, the amount may also be determined based on other factors. For example, if the member pays the pharmacy for the prescription drug without using the prescription or drug benefit provided by the PBM, the amount of money paid by the member may be higher than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a Wi-Fi network, or an IEEE 802.11 standards network, as well as various combinations thereof. The network 104 may include optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102, 106-110 or in parallel to link the devices 102, 106-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy device 106 may be utilized by the pharmacy to submit the claim to the PBM for adjudication.

Additionally, in some embodiments, the pharmacy device 106 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager device 102 may track prescription drug fulfillment and/or other information for patients that are not members or have not identified themselves as members, at the time (or in conjunction with the time) in which they seek to have a prescription filled at a pharmacy.

The pharmacy device 106 may include an order processing device 114, a pharmacy management device 116, and a pharmacy fulfillment device 112 in communication with each other directly and/or over the network 104.

The order processing device 114 may receive information regarding filling prescriptions and may direct an order component to one or more devices of the pharmacy fulfillment device 112 at a pharmacy. The fulfillment device 112 may fulfill, dispense, aggregate, and/or pack the order components of the prescription drugs in accordance with one or more prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the fulfilment device 112. In some embodiments, the order processing device 114 may be an external device separate from the pharmacy and communicate with other devices located within the pharmacy.

For example, the external order processing device 114 may communicate with an internal order processing device 114 and/or other devices located within the system 100. In some embodiments, the external order processing device 114 may have limited functionality (e.g., as operated by a patient requesting fulfillment of a prescription drug), while the internal pharmacy order processing device 114 may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together.

Generally, a prescription order is generated for a pharmacy. The prescription order may include more than one prescription drug for fulfillment. Each prescription drug in a prescription order is an order component of the prescription order. Generally, the order components are pill bottles, liquid bottles, blister packs, unit-of-use packs, injectable package, spray bottles, tubes, ampoules, drop counters, insulated boxes, child-resistant containers, or other packaging having a quantity of a prescription drug contained therein.

In some embodiments, the order processing device 114 may operate in combination with the pharmacy management device 116.

The order processing device 114 may include circuitry, a processor, a memory to store data and instructions, and communication functionality. The order processing device 114 is dedicated to performing processes, methods and/or instructions described herein. Other types of electronic devices specifically configured to implement with the processes, methods and/or instructions described herein may also be used.

In some embodiments, at least some functionalities of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage, etc.) and/or through the network 104 (e.g., by utilizing a cloud configuration or software as a service. etc.) with the storage device 110.

The user device 108 is used by a device operator. The device operator may be a user (e.g., an employee, a contractor, a benefit member, etc.) associated with a software development project. Other device operators may also operate the user device 108.

The user device 108 may be a stand-alone device that solely provides at least some of the functionality of the methods and systems, or may be a multi-use device that has functionality outside of analysis of the methods and systems. Examples of the user device 108 include a set-top box (STB), a receiver card, a mobile telephone, a personal digital assistant (PDA), a display device, a portable gaming unit, and a computing system, etc. Other devices, however, may also be used. In some embodiments, the computing system may include a mobile computing device. For example, the user device 108 may include a mobile electronic device, such an iPhone or iPad by Apple, Inc., mobile electronic devices powered by Android by Google, Inc., and a Blackberry by BlackBerry Limited. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, etc.) in communication with the benefit manager device 102, the pharmacy device 106, and/or the user device 108 directly and/or over the network 104. The non-transitory storage may store pharmaceutical data such as order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (e.g., drug name and strength, etc.) and quantity of the prescription drug, etc. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 118 may be used by a fulfillment center to fulfill a pharmacy order.

In some embodiments, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to transport prescriptions within the pharmacy may also be stored as order data 118.

The member data 120 includes information regarding the members associated with the PBM. The information stored as member data 120 may include personal information, personal health information, protected health information, and the like. Examples of the member data 120 include name, address, telephone number, e-mail address, prescription drug history, etc., and the like. The member data 120 may include a plan sponsor identifier that identifies the plan sponsor associated with the member and/or a member identifier that identifies the member to the plan sponsor. The member data 120 may include a member identifier that identifies the plan sponsor associated with the patient and/or a patient identifier that identifies the patient to the plan sponsor. The member data 120 may also include, by way of example, dispensation preferences such as type of label, type of cap, message preferences, language preferences, or the like.

The member data 120 may be accessed by various devices in the pharmacy (e.g., the fulfillment center, etc.) to obtain information utilized for fulfillment and shipping of prescription orders. In some embodiments, an external order processing device 114 operated by or on behalf of a member may have access to at least a portion of the member data 120 for review, verification, etc., or other purposes.

In some embodiments, the member data 120 may include information for persons who are patients of the pharmacy but are not members in the pharmacy benefit plan being provided by the PBM. For example, these patients may obtain drug directly from the pharmacy, through a private label service offered by the pharmacy, the fulfillment center, or otherwise. In general, the use of the terms member (e.g., of a prescription drug plan) and patient (e.g., of a pharmacy) may be used interchangeably herein.

The claims data 122 includes information regarding pharmacy claims adjudicated by the PBM under a drug benefit program provided by the PBM for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copay/coinsurance amount, rebate information, and/or member eligibility, and the like. Additional information may be included.

In some embodiments, other types of claims beyond prescription drug claims may be stored in the claims data 122. For example, medical claims, dental claims, wellness claims, or other type of health care-related claims for members may be stored as a portion of the claims data 122.

In some embodiments, the claims data 122 includes claims that identify the members with whom the claims are associated. In some embodiments, the claims data 122 includes claims that have been de-identified (e.g., associated with a unique identifier but not with a particular, identifiable member), aggregated, or otherwise processed.

The drug data 124 may include drug name (e.g., technical name and/or common name, etc.), other names by which the drug is known by, active ingredients, an image of the drug (e.g., in pill form, etc.), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc., and the like.

Figure 2:
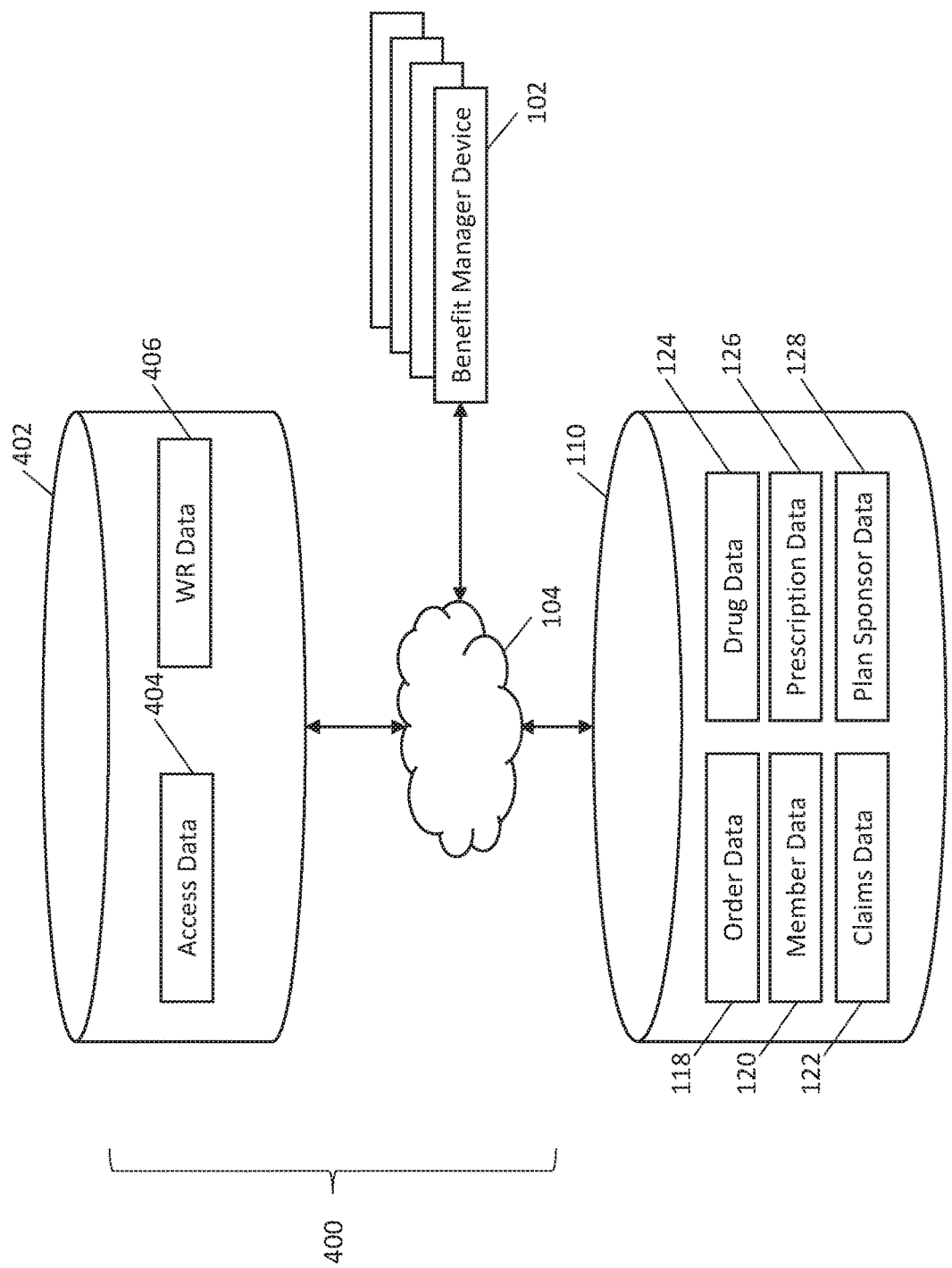
FIG. 2 is a block diagram of an example implementation of a system for controlling workflow of pharmaceutical data, according to an example embodiment.

FIG. 2 is a block diagram of an example implementation of a system 400 for controlling data workflow, according to an example embodiment. While the system 400 is generally described as being deployed for use in controlling workflow of work requests in updating or otherwise changing data, the system 400 and/or components thereof may otherwise be deployed.

The system 400 includes a single or multiple benefit manager devices 102 (see FIG. 1). The benefit manager devices 102 represent hardware circuitry that includes and/or is connected with one or more processors (e.g., microprocessors, field programmable gate arrays, integrated circuits, or the like) that operate to perform various operations to control the workflow of work requests, such as limiting operator access to only the portions of the pharmaceutical data that is associated with or needed to complete the work requests assigned to the operator, to link data representative of related work requests with each other and/or prevent the link to data representative of work requests from being performed out of order out of sequence with respect to each other, and/or identify or track changes to the pharmaceutical data in order to present or highlight the changes to the operator before the work request is completed and/or to a reviewer of the operators work (for example, during quality review).

The benefit manager device 102 communicate with the storage device 110 and/or one or more than one additional storage devices 402 (e.g., via the network 104) to access information used to determine which portions of the pharmaceutical data are needed to complete various work requests, which data representative of work requests are linked or otherwise associated with each other, and/or what changes the pharmaceutical data has occurred during completion or performance of one or more work requests. While the storage devices 110, 402 are shown as separate devices in FIG. 2, the storage devices 110, 402 may be combined into a single storage device or may be split among more than two storage devices 110, 402. In some embodiments, the storage devices 110, 402 may be referred to as memories of a computer system or computer memories.

The storage device 402 stores data used to determine the data of which work requests are linked or associated with each other, what portions of the pharmaceutical data is needed to complete various work requests, and/or data representative of changes to the pharmaceutical data or data indicative that changes to the pharmaceutical data has been made. In general, this data is separately stored in different data structures in the storage device 402 to allow for the quick and easy modification of which data of the work requests are linked with each other, which portions of the pharmaceutical data is needed to complete various work requests, and/or which portions of the pharmaceutical data have been modified during completion of one or more requests. Without separately storing the data in this or similar manner, determination of which data of the work requests are linked with each other, which data is needed to be accessed to complete various work requests, and/or which data has been modified during completion of various work requests can be a time-consuming, complex, and error-prone process. As such, the manner in which the data is stored improves performance of the computing system that accesses and utilizes such data.

Access data 404 may be stored in the additional storage device and represent data structures that associate different work requests with different subsets or portions of the pharmaceutical data. The order data 118, the member data 120, the claims data 122, the drug data 124, the prescription data 126, and/or the plan sponsor data 128 can be different subsets or portions of the pharmaceutical data. In some embodiments, one or more, or each, of the order data 118, the member data 120, the claims data 122, the drug data 124, the prescription data 126, and/or the plan sponsor data 128 can include subsets or portions of the pharmaceutical data. As one example, the names of members within the member data 120 can represent one subset or portion of the pharmaceutical data, the addresses of those members within the member data 120 can represent another, different subset or portion of the pharmaceutical data, and so on.

Different work requests may be associated with or restricted to different subsets or portions of the pharmaceutical data to prevent other subsets or portions of the pharmaceutical data that are not needed for completion of the work requests from being accessed or modified. For example, a work request may seek to change which medications are covered by a benefits plan in the claims data 122. This work request may be restricted to the claims data 122 (and/or one or more other subsets or portions of the pharmaceutical data, such as the member data 120 or a portion of the member data 120) to prevent an operator performing the work request from modifying other pharmaceutical data. For example, the operator may be prevented from changing a name or address of the member in the member data 120, from changing any of the plan sponsor data 128, from changing any of the member's prescriptions on file in the prescription data 126, or the like.

Work requests data 406 (WR data 406 in FIG. 2) may be stored in the additional storage device 402 and represent data structures that link or otherwise associate the data of different work requests with each other. Different work requests may be linked or associated with each other when the work requests are to be completed in a designated or dictated order or sequence. For example, a first work request seeking to change a surname of a person being added to a benefits plan may need to be completed prior to a second work request that adds the person to the benefits plan. The second work request may need to be completed prior to a third work request that adds the mailing address of the person added to the benefits plan. The performance of two or more of these work requests in a different order or sequence may create problems and/or inconsistencies within the pharmaceutical data. For example, attempting to add the person to the benefits plan (the second work request) prior to updating the surname of that person (the first work request) may result in the member data 120 and the plan sponsor data 128 having inconsistent or non-matching information stored therein for the same person. This error can result in the new member to the benefits plan being denied benefits, being provided with benefits different from those contracts agreed to, or other problems. As another example, the work requests may request changes to the data. These changes may be linked with each other by associating the work requests with each other in order to reduce or eliminate error in modifying the data. For example, two different work requests may ask operators to change the same or different data associated with the same pharmaceutical provider. The data changes sought by the work requests may be linked so that the performance or implementation of one work request may serve as a check or verification of the data change sought by another linked work request.

In some embodiments, the work request data 406 may include data structures that identify which portions or subsets of the pharmaceutical data were changed by completion of a work request and/or identify what changes were made to the subsets of the pharmaceutical data. For example, the data structures of the work request data 406 may indicate that the business address of a benefits plan sponsor in the plan sponsor data 128 was changed by an operator performing a work request. In some embodiments, the data structures of the work request data may include the new or changed address of the benefits plan sponsor in the plan sponsor data 128. This information may be used for presenting the previous and/or updated pharmaceutical data to the operator performing the work request for verification by the operator that the changes were accurately made. In some embodiments, this information may be used for presenting the previous and/or updated pharmaceutical data to a reviewer performing a quality review for checking on the accuracy of the work request completed by the operator. The pharmaceutical data that is changed by a work request may control or be used to control which prescription drug benefits, medical benefits, and/or other type of benefits are available to a member of one or more than one insurance or benefit plans.

FIG. 3 illustrates one example of a data structure 500 representative of the access data 404 and/or the work request data 406 shown in FIG. 2 according to an example embodiment. While the data structure 500 is represented in FIG. 3 graphically, it should be appreciated that the data structure 500 may be implemented in a computer system (e.g., in a file allocation table and data associated therewith) in memory, drive storage, and/or cloud storage, or otherwise implemented. The data structure 500 includes several records 502 each associated with a different work request. The records 502 each include several cells 504-526 including data representative of different information.

In some embodiments, the data of the cells 504-526 of the data structure is stored as binary data, hex data, or otherwise. When such data of the cells 504-526 are ultimately displayed (e.g., to a user of the system 400), the underlying data is interpreted, translated, or otherwise processed into a human readable level identifier.

The cells 504 include data that represent or indicate the type of work request. For example, the work request labeled "TOR A" can represent a work request that seeks to change a name and/or a company name member data 120. The work request labeled "TOR B" can represent a work request that seeks to change a benefit provided under a pharmacy benefits plan, such as by changing benefits coverage for medication in the claims data 122. The other work requests labeled "TOR C" and "TOR D" can represent other changes to different portions of the pharmaceutical data. The work request labeled "Report BC" and the work request labeled "Report ABC" can represent requested outputs or summaries of different types of pharmaceutical data, such as member names, claims, company names, insurance plans, or the like.

The cells 506 include data that represent or indicate an identification or identifier of the corresponding work request in the same record 502. The work request identifications or identifiers may be unique in that node to work requests may have the same identification number or identifier number. In some embodiments, two or more work requests may have the same identification or identifier, such as work requests that seek to change the same subset or portion of the pharmaceutical data.

The cells 508-520 include data that represent or indicate which portions or subsets of the pharmaceutical data are needed or are allowed to be accessed or changed during performance of the associated work request in the same record 502. In some embodiments, these cells 508-520 can include data that represent or indicate which portions or subsets of the pharmaceutical data are not needed or are not allowed to be accessed or changed during performance of the associated work request in the same record 502.

For example, the cells 508 can indicate which of the work requests need to access or can access the first portion or subset of the claims data 122. In the illustrated embodiment, the number "1" is included in the cell 508 for the work requests that are allowed to access or change the first subset or portion of the claims data 122. The number "0" may be included in the cell 508 for the work requests that are not allowed to access or change the first subset or portion of the claims data 122. In some embodiments, other data may be used to indicate which data subsets or portions may or may not be accessed for various work requests.

Other cells 510-520 can indicate which work requests are allowed or not allowed to access or change other portions or subsets of the pharmaceutical data. For example, the cells 510 may indicate which work requests are allowed to access or change a different, second subset of the claims data 122, the cells 512 can indicate which work requests are allowed to access or change a first subset or portion of the member data 120, the cells 514 indicate which work requests are allowed to access or change a different, second subset or portion of the member data 120, and the cells 516 indicate which work requests can change or access a different, third portion of the member data 120. The cells 518 can indicate which work requests are allowed to access or change a first portion of subset of the plan sponsor data 128, while the cells 520 indicate which work request are allowed to access or change a different, second portion or subset of the plan sponsor data 128. All the preceding examples focus on subsets or portions of the claims data 122, member data 120, and plan sponsor data 128, but one or more than one additional cell may be added to one or more of the records 502 in the data structure 500 to indicate which other portions or subsets of the pharmaceutical data may be accessed or changed by the corresponding work requests.

One or more of the benefit manager devices 102 may dictate the values in the cells 508, 510, 512, etc., based on designated or predetermined subsets of the pharmaceutical data that are allowed to be accessed or changed by different work requests. For example, the designation of which subsets or portions of the pharmaceutical data may be accessed by different work requests may be programmed or stored into the access data 404 by the benefit manager devices 102 based on a manager or supervisor input.

In operation, one or more than one operator may use the benefit manager devices 102 to change the subsets of the pharmaceutical data based on work requests assigned to the operators. An operator may begin work on a work request by selecting the work request on a user interface (e.g., a display device) of the benefit manager device 102. The benefit manager device 102 queries the data structure 500 to determine which of the subsets of pharmaceutical data can be access by and/or modified by the operator performing the work request.

The operator may be presented with some, but not all, of the pharmaceutical data stored in the data storage device 110 responsive to selecting or initiating the work request. The portion of the pharmaceutical data that is shown (or categories of the pharmaceutical data that are shown) to the operator may be restricted to those subsets of the pharmaceutical data that are associated with the work request. The benefit manager device 102 may examine the record 502 of the work request assigned to the operator to determine which cells 508-520 include data indicating that a corresponding subset of the pharmaceutical data can be accessed or modified by the operator during performance of the work request.

With respect to the example shown in FIG. 3, an operator working on the work request labeled "TOR B" (having the identifier 33152 in the cell 506) may be allowed to access or modify data in the first and second subsets of the claims data 122 and the first and third subsets of the member data 120, but may not be allowed to access or modify data in the other subsets of the claims data 122, member data 120, or plan sponsor data 128. This operator may view and/or modify the pharmaceutical data within the allowed subsets to perform the work request.

Upon completion of the work request, the same operator may switch to another work request. This other work request may be associated with different subsets of the pharmaceutical data than the previous work order. For example, the operator may begin working on the work request labeled "Report ABC." The benefit manager device 102 queries the data structure 500 to determine which of the subsets of pharmaceutical data can be access by and/or modified by the operator performing the work request. As shown in the cells 508-520, this work request is associated with, and allows operator access to, the first subset of the claims data 122 (e.g., cell 508), the second and third subsets of the member data 120 (e.g., cells 514, 516), and the first subset of the plan sponsor data 128 (e.g., cell 518). However, the work request does not allow the operator to access or change data in the other subsets represented by the cells 510, 512, 520). This operator may view and/or modify the pharmaceutical data within the allowed subsets to perform the work request.

The data structure 500 that is representative of the access data 404 may, in some embodiments, include additional cells 522-526 that indicate how the data of some work requests are linked with each other and/or current statuses of the work requests. The data included in the cells 522 of the data structure 500 include a group identifier. Data representative of work requests having the same group number in the cell 522 may be linked with each other. In the illustrated example, the work requests labeled "TOR A," "TOR B" (having the identifier 33152 in the cell 506), and "Report BC" have the same group identifier value in the cells 522 of the corresponding records 502. This common group identifier in the cells 522 indicates that the data of these work requests are linked together.

Similarly, the work requests labeled "TOR C" and "Report ABC" have the same group identifier in the cells 522 of the corresponding records 502 in the data structure 500. This indicates that the data of these work requests are linked together or included in a common group.

The cells 524 in the records 502 of the data structure 500 can be used to store data that indicates a sequence or order in which the linked data of the work requests are to be completed. With respect to the linked data of the work requests labeled "TOR A," "TOR B" (having the group identifier 33152), and "Report BC," the cells 524 in the data structure 500 indicate that the work request labeled "TOR B" is to be completed first, the work request labeled "TOR A" is to be completed after the work request labeled "TOR B" (but not necessarily consecutively as one or more other work requests may be performed there between), and the work request labeled "Report BC" is to be completed after the work request labeled "TOR A" (but not necessarily consecutively as one or more other work requests may be performed there between).

With respect to the linked work requests labeled "TOR C" and "Report ABC," the cells 524 do not indicate any relative priority, order, or sequence in which the linked data of these work requests need to be processed. Instead, the linking of the data of these work requests may indicate that the work requests are to be completed consecutively. For example, the benefit manager devices 102 may examine the cells 524 and notify operators to complete the work requests having the linked data one right after another, but in any order. For example, if an operator completes the work request labeled "TOR C," a user interface of the benefit manager device 102 used by the operator may display or present a notification instructing the operator to then begin work on the linked work request labeled "Report ABC."

As another example, if a first operator working on a first benefit manager device 102 completes the work request labeled "Report ABC," then a different, second operator working on a different, second benefit manager device 102 may be notified, instructed, or automatically begin work on the linked work request labeled "TOR C" based on the common group identifiers in the cells 522.

The linking of the work requests in the cells 522 of the data structure 500 allows for different operators working on different benefit manager devices 102 to maintain the linking of the work requests even if the operators are unaware of each other's work. This linking can ensure that the work requests are completed in the sequence of work requests, or are completed together, to avoid inconsistencies or inaccuracies in the pharmaceutical data being accessed or modified by the work requests.

The reports 502 in the data structure 500 may include the cells 526, which indicate completion of the work requests. The data included in the cells 526 can be queried or examined by the benefit manager devices 102 to determine whether a work request has been completed or not. For example, the benefit manager device 102 may examine cell 526 in a record 502 of a work request to determine if the data included in that cell 526 indicates that the corresponding work request identified in the cell 504 or 506 of the same record 502 has been completed or is yet to be completed. In the illustrated example, the cells 526 in the records 502 for the work request labeled "TOR B" (having a group identifier 33152 in the cell 506) and the work request labeled "TOR C" have been completed. For example, a value of one in the cells 526 can represent completion of the corresponding work request, while a value of zero indicate that the corresponding work request has not been completed.

The benefit manager devices 102 may examine the cells 526 to determine if and/or when linked work requests can be completed or performed. In the illustrated example, for the work requests having the group identifier value of 395, the values of the data in the cells 526 can indicate that the first work request labeled "TOR B" in the sequence of linked work requests associated with the group identifier 395 has been completed, but that the other work requests in the group 395 have not been completed. The benefit manager device 102 may then allow an operator to perform or begin work on the work request labeled "TOR A" of the group 395 because the first work request labeled "TOR B" in the group 395 has been completed, but will not allow the operator to begin work on the third work request labeled "Report BC" in the group 395, due to the relative priority, order, or sequence of these linked work requests (as reflected by the data in the cells 524).

The data structure 500 may represent a combination of data structures stored in the storage device 402 as the access data 404 and/or the work request data 406. For example, the access data 404 may include a record for each work request and several cells indicating which subsets of the pharmaceutical data that can be accessed when performing the work request. However, the access data 404 may include data structures that include different information than what is shown in FIG. 3. For example, the data structures of the access data 404 may not include cells containing data representative of links between work requests, sequences or orders of the linked work requests, and/or current statuses of the work requests.

FIG. 4 illustrates one example of a data structure 600 representative of the work request data 406 shown in FIG. 2 according to one example embodiment. While the data structure 600 is represented in FIG. 4 graphically, it should be appreciated that the data structure 600 may be implemented in a computer system (e.g., in a file allocation table and data associated therewith) in memory, drive storage, and/or cloud storage, or otherwise implemented.

The data structure 600 includes several records 602 each associated with a different work request and/or different versions of the same work request. The records 602 each include several cells 604-620 including data representative of different information.

In some embodiments, the data of the cells 604-626 of the data structure is stored as binary data, hex data, or otherwise. When such data of the cells 604-626 are ultimately displayed (e.g., to a user of the system 400), the underlying data is interpreted, translated, or otherwise processed into a human readable level identifier.

The cells 604 include data representative of the name or type of work request for the corresponding record 602, similar to the cells 504 in the data structure 500 shown in FIG. 3. Each work request in the data structure 600 may be associated or represented by two records 602. One record may include the values of the pharmaceutical data prior to completion of the work request (referred to as the current or live version of the data) while the other record may include the values of the pharmaceutical data after completion of the work request (referred to as the work in progress, or WIP, data). For example, the record 602 with the work request labeled "TOR A (Live)" in the cell 604 and the record 602 with the work request labeled "TOR A (WIP)" in the cell 604 may be the same work request. The cells 608, 610, 612, 614, 616, 618, 620 include values of the pharmaceutical data. For example, the values of the pharmaceutical data in the cells 608-620 for the record 602 associated with the work request labeled "TOR A (Live)" can be the current or live version of the pharmaceutical data, while the values of the pharmaceutical data in the cells 608, 610, 612, 614, 616, 618, 620 for the record 602 associated with the work request labeled "TOR A (WIP)" may be the WIP version of the pharmaceutical data.

In the illustrated example of FIG. 4, the work request labeled "TOR A" changes the value of the pharmaceutical data in the first subset of the member data (e.g., cell 614) from "Jane Doe" to "Jane Smith." The "Jane Smith" value of the member data is contained in the cell 614 for the record associated with the record 602 associated with the work request labeled "TOR A (WIP)." This work request also changes the value of the third member data contained in the cells 618 from "Company B" to "Company A."

Also shown in FIG. 4 are the current and WIP values of the first subset of the claims data (e.g., in the cells 608) for the work request labeled "TOR B." The current or live version of this claims data is a value of "1" while the updated or WIP version of the claims data is a value of "0." This indicates that the work request labeled "TOR B" was used to change the value of the first subset of the claims data from a value of 1 to a value of 0.

The data structure 600 may be used by the benefits manager device 102 to determine what pharmaceutical data was changed by a work request, and optionally the WIP value of the pharmaceutical data. An operator or reviewer (e.g., a person reviewing or performing a quality review of the work request performed by an operator) may use the benefit manager device 102 to examine the data structure 600 to determine which subset or portion of the pharmaceutical data was changed by a work request and/or the updated (WIP) value of the subset or portion of the pharmaceutical data that was changed.

Based on the information included in the data structure 600, the benefit manager device 102 can present a summary of at least some of the pharmaceutical data, with the WIP subset or portion of the pharmaceutical data highlighted, presented in different text (e.g., different colored text, larger text, bold text, underlined text, italic text, or the like) than other pharmaceutical data so that the operator or reviewer can easily see which portion of the pharmaceutical data has been changed and the changed value of this portion of the pharmaceutical data.

The operator or reviewer can then decide whether the change to the pharmaceutical data is correct and, responsive to determining that the change is correct, provide input to the benefit manager device 102 to save the WIP version of the pharmaceutical data as the current or live version of the pharmaceutical data. However, if the operator or reviewer decides that the change is not correct, then the operator or reviewer can provide input to the benefit manager device 102 to not save the WIP version of the pharmaceutical data as the current or live version of the pharmaceutical data.

FIG. 5 illustrates one example of a GUI 700 presented on a user interface by a benefit manager device 102 according to one example embodiment. The GUI 700 can be presented to summarize the change to the pharmaceutical data implemented by completion of a work request, such as the work request labeled "TOR A" in the data structure 600 shown in FIG. 4. The GUI 700 may be generated by the benefit manager device 102 so that the operator or a reviewer can examine the WIP data of the pharmaceutical data that was changed by the work request and determine if the change is correct. The GUI 700 illustrates the changes to the first and third subsets of the member data by displaying text 702, 704 representative of the WIP values of the first and third subsets of the member data.

The text 702, 704 may differ from text 706 representative of live pharmaceutical text that is not changed by the work request. In the illustrated example, the text 702, 704 of the WIP pharmaceutical data is shown in bold, italic, and in some embodiments different colored text relative to the text 706 of the live pharmaceutical data. The GUI 700 provides a summary of the results of the work request so that the operator or reviewer can quickly and easily see the changes made by the work request and, if needed, to reject incorrect changes to the pharmaceutical data caused during performance of the work request.

FIG. 6 illustrates another example of a GUI 800 presented on a user interface by a benefit manager device 102 according to one example embodiment. Similar to the GUI 700, the GUI 800 can be presented to summarize the change to the pharmaceutical data implemented by completion of the work request labeled "TOR B" in the data structure 600 shown in FIG. 4. The GUI 800 may be generated by the benefit manager device 102 so that the operator or a reviewer can examine the WIP data of the pharmaceutical data that was changed by the work request and determine if the change is correct. The GUI 800 illustrates the change to first subset of the claims data displaying text 802 representative of the WIP value of the first subset of the claims data.

The text 802 may differ from text 806 representative of live pharmaceutical text that is not changed by the work request. In the illustrated example, the text 802 of the WIP pharmaceutical data is shown in bold, italic, and in some embodiments different colored text relative to the text 806 of the live pharmaceutical data. The GUI 800 provides a summary of the results of the work request so that the operator or reviewer can quickly and easily see the changes made by the work request and, if needed, to reject incorrect changes to the pharmaceutical data caused during performance of the work request.

Figure 7:
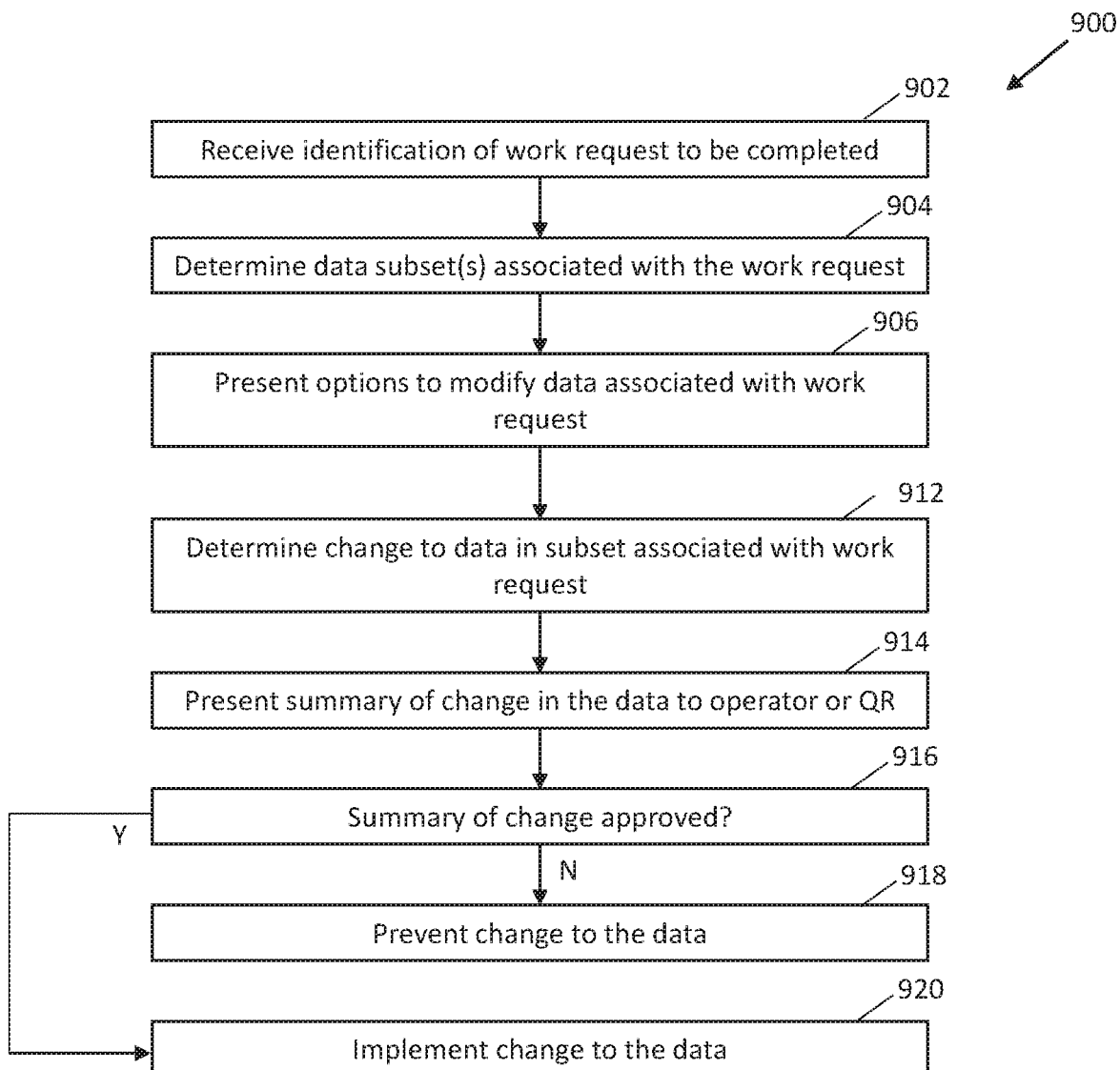
FIG. 7 is an example process flow illustrating a method for configuring data storage devices for use in controlling access to subsets of pharmaceutical data according to an example embodiment.

FIG. 7 is an example process flow illustrating a method 900 for configuring data storage devices for use in controlling access to subsets of pharmaceutical data according to an example embodiment. The method 900 may be used to create and/or use the data structures 500, 600 stored in one or more than one of the storage devices 110, 402 described above.

At block 902, an identification of a work request to be completed is received. For example, the benefit manager device 102 may receive input from an operator indicating a work request that is to be completed in order to examine or change the pharmaceutical data.

At block 904, one or more than one subsets of the pharmaceutical data are identified as or are determined to be associated with the work request. The benefit manager device 102 can examine the data structure 500 (e.g., the cells 508, 510, 512, etc., of the record 502 associated with the work request) to determine which of the subsets of the pharmaceutical data can be accessed by the operator during performance of the work request determined at block 902.

At block 906, one or more than one option to modify data in the subset(s) of pharmaceutical data associated with the work request are presented to the operator (e.g., through a user interface). The benefit manager device 102 may examine the data structure 500 to identify which subsets of the pharmaceutical data are associated with the work request and direct a user interface to present these subsets (or options to change the data in these subsets). As one example, the benefits manager device 102 can present windows configured to receive text entries, drop-down menus, or the like, on a GUI that the operator can use to enter or change data in the subsets of the pharmaceutical data associated with the work request.

As one example, if a work request is associated with first and second subsets of plan sponsor data, but is not associated with a third subset of plan sponsor data or any portion of the member data, the benefit manager device 102 may determine that the first and second subsets, but not the third subset, are to be available or presented to the operator.

The benefit manager device 102 may not allow the operator to view and/or modify the portions of the pharmaceutical data not associated with the work request in one embodiment. In some embodiments, the benefit manager device 102 may allow the operator to view the data not associated with the work request, but may not allow the operator to change the data. The method 900 may then terminate, or may return toward another operation, such as the operations performed at block 902.

At decision point 912, one or more than one change to the data in the subset(s) associated with the work request are determined. These operations may include the benefit manager device 102 examining the input provided by the operator via the input devices (e.g., keyboards, touchscreens, styluses, or the like). The benefit manager device 102 can create or modify one or more than one of the data structures to record the change(s) to the data in the subsets associated with the work request. For example, the benefit manager device 102 can add or modify the WIP work request in the data structure 600 to include the modifications to the data provided by the operator. The change in the data can be determined by comparing the previous (e.g., live) version of the pharmaceutical data in the data structure 600 with the modified (e.g., WIP) version of the pharmaceutical data in the data structure 600. Non-matching components of the live data and the WIP data can indicate the change made by the operator.

At block 914, a summary of the change to the pharmaceutical data provided by the operator is presented to the operator or to a quality reviewer. This summary can be presented via a user interface to the operator or a reviewer performing a quality review of the work performed by the operator. The summary can distinguish (e.g., highlight) the change made by the operator (determined at decision point 912) by changing an appearance of the changed data in the GUI relative to other data presented in the GUI, as described above.

At decision point 916, a determination is made as to whether the summary of the change(s) made by the operator to the data are approved. This determination can include the benefit manager device 102 examining input provided by the operator or reviewer via the input devices. If the input indicates acceptance or approval of the changes to the data, then flow of the method 900 can proceed to block 920. However, if the input indicates denial of the changes to the data, then the operator or reviewer may be refusing the changes to the data as being incorrect or otherwise unacceptable. As a result, flow of the method 900 can proceed to block 918.

At block 918, the change to the pharmaceutical data provided by the operator is prevented. This can involve the benefit manager device 102 not changing the live version of the pharmaceutical data as directed by the WIP version of the pharmaceutical data entered by the operator. The change(s) to the data entered by the operator may be discarded (e.g., erased).

At block 920, the change to the pharmaceutical data provided by the operator is implemented. This implementation can involve the benefit manager device 102 changing some or all of the live version of the pharmaceutical data to match the WIP version of the pharmaceutical data entered by the operator.

Flow of the method 900 can terminate following the operations performed at block 918 or block 920, or, in some embodiments, may return to one or more than one other operations, such as those performed at block 902.

Figure 8:
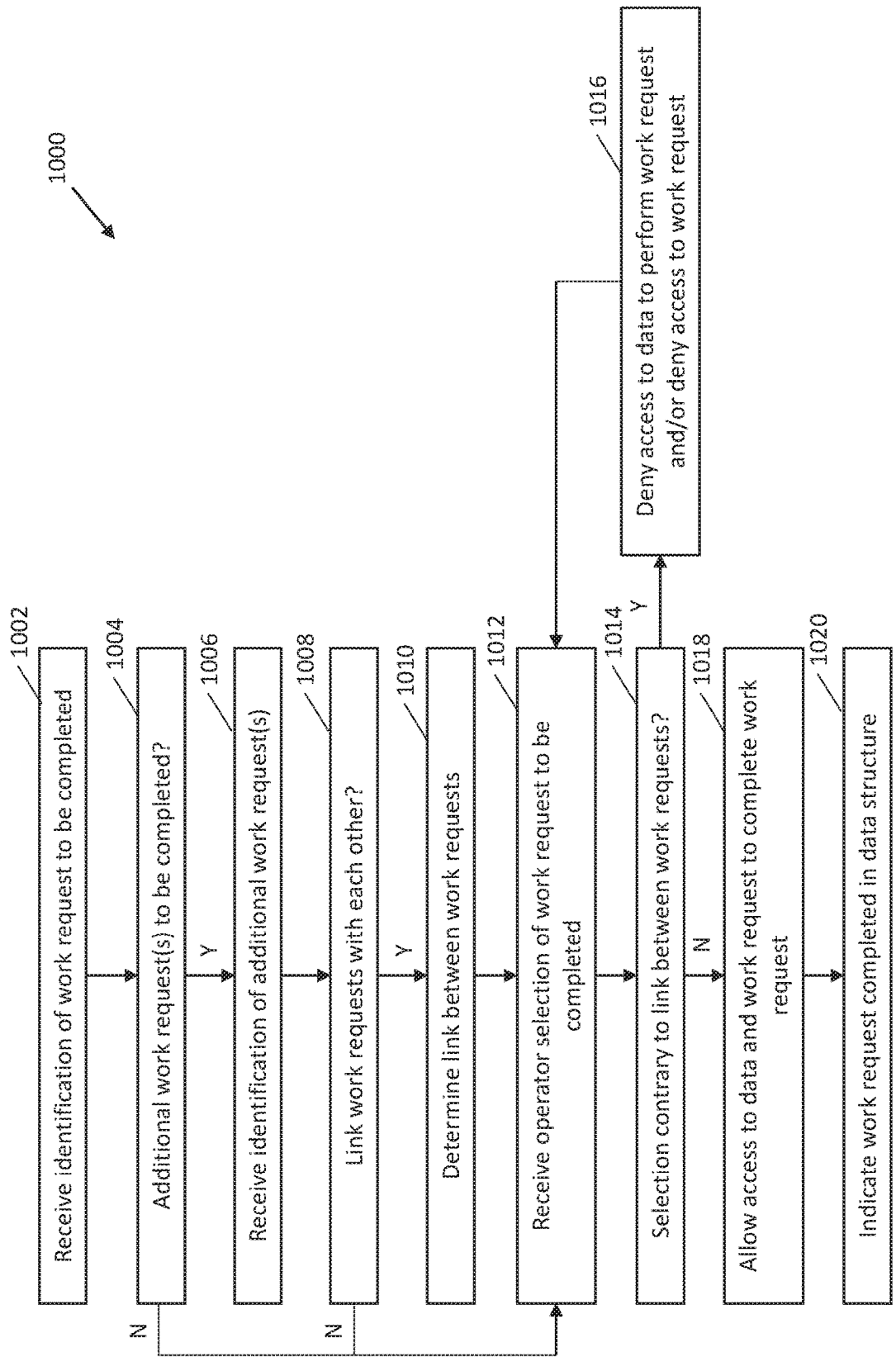
FIG. 8 is an example process flow illustrating a method for configuring data storage devices for use in controlling workflow of pharmaceutical data according to an example embodiment.

FIG. 8 is an example process flow illustrating a method 1000 for linking data of work requests for use in controlling data workflow according to an example embodiment. The method 1000 may be used to create and/or use the data structures 500, 600 stored in the storage devices 110, 402 described above. The method 1000 can be performed to determine which work requests are linked with each other and/or to control how the linked work requests are performed.

At block 1002, identification of a work request to be completed is received. The benefit manager device 102 may receive this identification from an operator via one or more than one user interfaces. The identification may be provided by the operator indicating the name of a work request, a unique identifier of the work request, or the like.

At decision point 1004, a determination is made as to whether any additional work requests are to be completed. The benefit manager device 102 may examine input provided by the operator via the input device to determine if the operator is entering one or more than one additional work requests. If such additional work requests are to be entered, then flow of the method 1000 can proceed toward block 1006. However, if no additional work requests are being entered by the operator (e.g., to be performed by this or another operator), then flow of the method 1000 can proceed to block 1012.

At block 1006, the identification of one or more than one additional work requests to be completed is received. The benefit manager device 102 may receive this identification from an operator via the input devices. The identification may be provided by the operator indicating the name of a work request, a unique identifier of the work request, or the like.

At decision point 1008, a determination is made as to whether two or more of the work requests are to be associated with each other, such as by linking the work requests with each other. This determination may be made by the benefit manager device 102 receiving input from an operator via the input devices. For example, the benefit manager device 102 can display a question or request to the operator on a display device asking whether any of the work requests are to be linked with each other. If the input received from the operator indicates that two or more of the work requests are to be linked with each other, then flow of the method 1000 can proceed to block 1010. Otherwise, flow of the method 1000 can proceed to block 1012.

At block 1010, the link between two or more of the work requests is determined. The operator may provide instructions to link one work request with another such that the work requests are required by the system 400 to be performed sequentially, in a designated order, and/or otherwise. These instructions may be received by the benefit manager device 102 via the input devices and examined by the benefit manager device 102 to determine how the work requests are linked. For example, the instructions may indicate that two or more of the work requests are to be completed by the same operator, are to be completed sequentially (without requiring the work requests to be completed in any particular order), are to be completed in a particular order (without requiring that the work request be completed sequentially, and/or are to be completed sequentially (e.g., one right after the other) and in a particular order.

The linking of work request performance may improve processor and/or system performance due to the inter-relationships of the different subsets of the pharmaceutical data. As one example, the linked work requests may be more efficiently completed together (regardless of the order) because the work requests make the same or substantially similar change to different portions of the pharmaceutical data. This can involve changing the same company address or name in the member data 120, claims data 122, and/or plan sponsor data 128. Because the pharmaceutical data may be organized into the different subsets due to the different functions performed using the different data subsets, the same change may be made to different subsets of the pharmaceutical data. In order to ensure that this repetitive change is made accurately, the system 400 may link the work requests so that the same operator performs the work requests and/or so that the work requests are completed one right after the other.

In another example, the linked work requests may be linked because the change to one subset of the pharmaceutical data as requested by one work request may not be possible or able to be made until a change to the same or another subset of the pharmaceutical data is completed. For example, member data 120 may need to be changed to reflect a change in a surname, a change in family status (e.g., recent marriage, recent birth of a child, etc.), or the like, prior to changing the plan sponsor data 128 to reflect the addition of a person to an insurance plan.

The method 1000 may repeat some or all of the operations described in connection with block 1002, decision point 1004, block 1006, decision point 1008, and block 1010 one or multiple times so that different groups or sets of work requests are entered into the system 400 and/or so that the links between two or more work requests are determined.

At block 1012, a selection of a work request is received. The benefit manager device 102 may receive input from an operator via the input devices indicating a work request that the operator wants to complete next. At decision point 1014, a determination is made as to whether the selected work request is contrary to or violates a link between two or more of the work requests. For example, if a first request is to be completed prior to a second work request and the operator selects the second work request for completion prior to the first work request, then the selection of the second work request is contrary to or in violation of the link between the first and second work requests. As another example, if third, fourth, and fifth work requests are to be completed sequentially but the operator selects a sixth work request for completion immediately after completion of the third work request (and prior to completing the fourth or fifth work request), then the selection may be contrary to or in violation of the link between the work requests.

If the work request selection is contrary to the link(s), then flow of the method 1000 can proceed to block 1016. However, if the selection is not contrary to or in violation of the link(s) between the work requests, then flow of the method 1000 can proceed to block 1018. If the operator selects a work request that is not linked to another work request and the selected work request does not violate or run contrary to link(s) between work requests, then the method 1000 can proceed to block 1018.

The determination of whether the selection is contrary to the link between the work requests can be performed at decision point 1014 by the benefit manager device 102 examining the data contained in the cells of the data structure 500. For example, the benefit manager device 102 can examine the data in the cells 522 to determine which work requests are linked with each other, can examine the data in the cells 524 to determine whether there is an order in which to complete the work requests, and/or can examine the data in the cells 526 to determine which work requests have been completed to determine which remaining linked work requests, if any, are to be completed next (e.g., prior to completing another, non-linked work request).

At block 1016, access to the selected work request and/or access to the subset of the pharmaceutical data needed to complete the selected work request is denied. The benefit manager device 102 can prevent the operator from working on the work request that is contrary to the link(s) between work requests. The benefit manager device 102 may prevent implementation of any change to the pharmaceutical data that is not part of a linked work request unless the selected work request complies with the link(s) between the work requests. Flow of the method 1000 can return to block 1012 to allow the operator to select another work request. In some embodiments, the method 1000 may then terminate.

At block 1018, access to the selected work request and/or access to the subset of the pharmaceutical data needed to complete the selected work request is allowed. The benefit manager device 102 can allow the operator to work on the selected work request because the work request complies with the link(s) between work requests. The benefit manager device 102 may implement change(s) to the pharmaceutical data that is part of the selected work request. As described above, this change may be stored in the data structure 600 as a WIP version of the data unless or until the operator or a reviewer approves the change.

At block 1020, the completion of the work request is indicated in the data structure. The benefit manager device 102 may change the value of the cell 526 for the record 502 associated with the completed work request in the data structure 500 to indicate that the work request has been completed. Flow of the method 1000 may return to block 1002 or another operator. In some embodiments, the method 1000 may then terminate.

Figure 9:
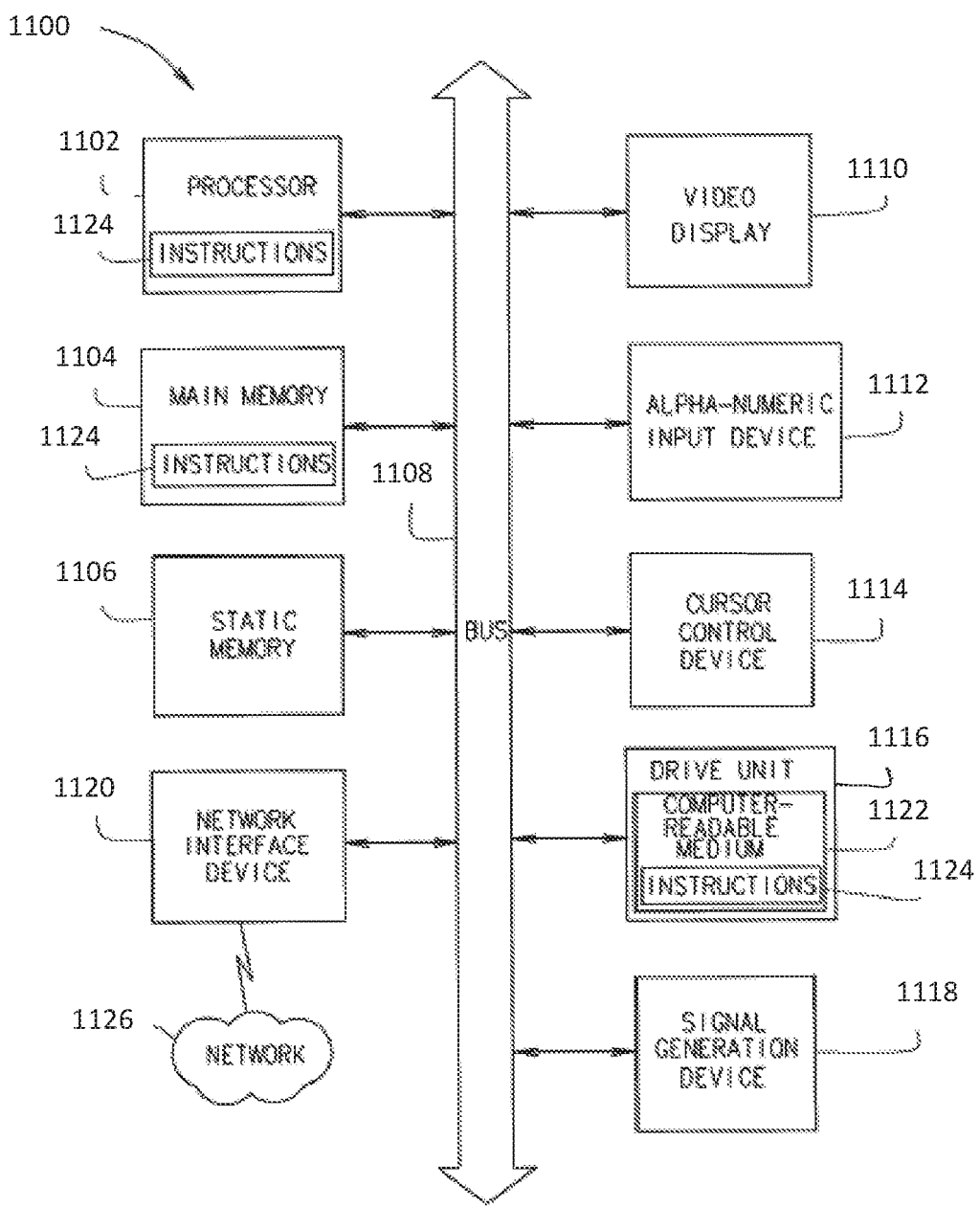
FIG. 9 shows a block diagram of a benefit manager device (shown in FIG. 1) in the example form of a computer system within which a set of instructions may be executed causing the machine to perform any one or more than one methods, processes, operations, or methodologies discussed herein.

FIG. 9 shows a block diagram of a benefit manager device 102 (shown in FIG. 1) in the example form of a computer system 1100 within which a set of instructions may be executed causing the machine to perform any one or more than one methods, processes, operations, or methodologies discussed herein. The devices 102, 108, 206-230, for example, may include the functionality of the one or more than one computer systems 1100. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 1100 includes one or more processors 1102 (e.g., a central processing unit (CPU), a graphics processing unit (GPU) or both, etc.), a main memory 1104 and a static memory 1106, which communicate with each other via a bus 1108. The computer system 1100 further includes a video display unit 1110 (e.g., a liquid crystal display (LCD) or a cathode ray tube (CRT), etc.). The computer system 1100 also includes an alphanumeric input device 1112 (e.g., a keyboard, etc.), a cursor control device 1114 (e.g., a mouse, etc.), a drive unit 1116, a signal generation device 1118 (e.g., a speaker, etc.) and a network interface device 1120.

The drive unit 1116 includes a computer readable medium 1122 on which is stored one or more than one sets of instructions 1124 (e.g., software, etc.) embodying any one or more than one methodologies or functions described herein.

The instructions 1124 may also reside, completely or at least partially, within the main memory 1104 and/or within the processor 1102 during execution thereof by the computer system 1100, the main memory 1104 and the processor 1102 also constituting non-transitory computer readable media. When loaded with the instructions 1124, the processor 1102 is a machine dedicated to only the present processes and methodologies.

The instructions 1124 may further be transmitted or received over a network 1126 via the network interface device 1120.

While the computer-readable medium 1122 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present invention. The term "Computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and subsystems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

The inventive subject matter may be represented in a variety of different embodiments of which there are many possible permutations.

In an example embodiment, method includes configuring one or more memories of a computer system according to a logical data structure having plural records that include first and second sets of cells. The first set of cells identify different work requests to change pharmaceutical data used to control pharmacy benefits to one or more insurance plan members. The second set of cells identify one or more subsets of the pharmaceutical data associated with completing one or more of the work requests. The one or more memories are configured to be queried to determine whether to prevent an operator from accessing one or more subsets of the pharmaceutical data other than the one or more subsets of the pharmaceutical data associated with completing a selected work request of the work requests to change the pharmaceutical data.

In another example embodiment, a system includes one or more processors configuring one or more memories of a computer system according to a logical data structure having plural records that include first and second sets of cells. The first set of cells identify different work requests to change pharmaceutical data used to control pharmacy benefits to one or more insurance plan members. The second set of cells identify one or more subsets of the pharmaceutical data associated with completing one or more of the work requests. The one or more processors are configured to query the logical data structure to determine whether to prevent an operator from accessing one or more subsets of the pharmaceutical data other than the one or more subsets of the pharmaceutical data associated with completing a selected work request of the work requests to change the pharmaceutical data.

In another example embodiment, a method includes configuring one or more memories of a computer system according to a logical data structure having plural records that include first and second sets of cells. The first set of cells identifies different work requests to change pharmaceutical data used to control pharmacy benefits to one or more insurance plan members. The second set of cells logically links two or more of the work requests with each other. The one or more memories are configured to be queried to determine a sequence in which the two or more work requests are to be completed.

In another example embodiment, a system includes one or more processors configuring one or more memories of a computer system according to a logical data structure having plural records that include first and second sets of cells. The first set of cells identify different work requests to change pharmaceutical data used to control pharmacy benefits to one or more insurance plan members. The second set of cells logically link two or more of the work requests with each other. The one or more processors are configured to query the one or more memories to determine a sequence in which the two or more work requests are to be completed.

Thus, methods and systems for controlling data workflow have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A method comprising:
  receiving a data access request, at a computing system, for completion of a group of data processing tasks by different system requestors using the computing system, a first data process task and a second data processing task directing modification of pharmaceutical data in a pharmacy benefit plan by the different system requestors;
  determining a logical link between the data processing tasks in the group, the logical link dictating a sequence in which the data processing tasks are to be completed by the different system requestors;
  accessing a plurality of first document types associated with the data processing tasks, the plurality of first document types indicating which of various subsets of the pharmaceutical data are required to complete the data processing tasks;
  accessing a plurality of second document types that indicate assignments of the data processing tasks to the system requestors;
  restricting access to the subsets of the pharmaceutical data based on the plurality of first document types and the assignments of the data processing tasks to the system requestors; and
  executing the data processing tasks in the sequence dictated by the logical link and based on the plurality of first document types and the plurality of second document types, wherein the second task of the data processing tasks is subsequent to the first task of the data processing tasks in the sequence dictated by the logical link with the second task prevented from being executed until completion of the first task.

2. The method of claim 1, wherein executing the first data processing task changes one or more pharmacies included in a pharmacy network of the pharmacy benefit plan.

3. The method of claim 1, wherein executing the first task changes identifying information about a pharmacy in the pharmacy benefit plan.

4. The method of claim 1, further comprising:
  receiving a data review request at the computing system;
  accessing a plurality of fourth document types that indicate a change to the pharmaceutical data due to execution of the first task; and
  presenting the change to the pharmaceutical data and one or more portions of the pharmaceutical data left unchanged by execution of the first data processing task.

5. A tangible and non-transitory computer readable storage medium comprising instructions that direct at least one processor to:
receive a data access request for completion of a group of data processing tasks by different system requestors using a computing system, a first data processing task and a second data processing task directing modification of pharmaceutical data in a pharmacy benefit plan by the different system requestors;
determine a logical link between the data processing tasks in the group, the logical link dictating a sequence in which the data processing tasks are to be completed by the different system requestors;
access a plurality of first document types associated with the data processing tasks, the plurality of first document types indicating which of various subsets of the pharmaceutical data are required to complete the data processing tasks;
access a plurality of second document types that indicate assignments of the data processing tasks to the system requestors;
restrict access to the subsets of the pharmaceutical data based on the plurality of first document types and the assignments of the data processing tasks to the system requestors; and
execute the data processing tasks in the sequence dictated by the logical link and based on the plurality of first document types and the plurality of second document types, wherein the second task of the data processing tasks is subsequent to the first task of the data processing tasks in the sequence dictated by the logical link with the second task prevented from being executed until completion of the first task.

6. The computer readable storage medium of claim 5, wherein execution of the first data processing task changes one or more pharmacies included in a pharmacy network of the pharmacy benefit plan.

7. The computer readable storage medium of claim 5, wherein execution of the first task changes identifying information about a pharmacy in the pharmacy benefit plan.

8. The computer readable storage medium of claim 5, wherein the instructions also direct the at least one processor to:
receive a data review request at the computing system;
access a plurality of fourth document types that indicate a change to the pharmaceutical data due to execution of the first task; and
present the change to the pharmaceutical subsets data and one or more portions of the pharmaceutical data left unchanged by execution of the first data processing task.

9. A method comprising:
receiving a data access request, at a computing system, for completion of a group of first data processing tasks by different system requestors using the computing system;
accessing a plurality of first document types associated with the first data processing tasks the plurality of first document types indicating which subsets of pharmaceutical data in a pharmacy benefit plan are required to complete the first data processing tasks, wherein the first data processing tasks request changes to a common subset of the subsets of the pharmaceutical data;
accessing a plurality of second document types that indicate assignments of the first data processing tasks to the different system requestors;
accessing a plurality of third document types that indicate requirements for sequential completion of the first data processing tasks;
preventing execution of any second data processing task between the first data processing tasks until execution of the first data processing tasks in any sequence is completed; and
executing the first data processing tasks based on the plurality of first document types and the plurality of second document types.

10. The method of claim 9, wherein executing the first data processing task changes one or more pharmacies included in a pharmacy network of the pharmacy benefit plan.

11. The method of claim 9, wherein executing the first data processing task changes identifying information about a pharmacy in the pharmacy benefit plan.

12. The method of claim 9, further comprising:
receiving a data review request at the computing system;
accessing a plurality of fourth document types that indicate a change to the subsets of the pharmaceutical data due to execution of the first data processing tasks; and
presenting the change to the subsets of the pharmaceutical data and one or more portions of the pharmaceutical data left unchanged by execution of the first data processing tasks.

13. The method of claim 12, further comprising:
receiving a confirmation indicator in response to presenting the change to the subsets of the pharmaceutical data, wherein the confirmation indicator represents acceptance of the change to the subsets of the pharmaceutical data.

14. The method of claim 1, further comprising:
storing multiple copies of the pharmaceutical data that is modified by the first task and the second task, a first copy of the copies of the pharmaceutical data including the pharmaceutical data before execution of the first task, a second copy of the copies of the pharmaceutical data including the pharmaceutical data after execution of the first task, wherein the second task involves reviewing the pharmaceutical data that is changed; and
displaying a first portion of the pharmaceutical data that is changed by the first task differently from a second portion of the pharmaceutical data that is not changed by the first task to at least one of the system requestors performing the second task.

15. The method of claim 1, wherein the second task involves reverting the modification to the pharmaceutical data to restore the pharmaceutical data that was changed to a prior version of the pharmaceutical data.

16. The method of claim 1, wherein access to the pharmaceutical data is restricted by displaying only the subsets of the pharmaceutical data that are assigned to the system requestors.

17. The method of claim 1, wherein the sequence in which the data processing tasks are to be completed includes at least third and fourth tasks required to be completed consecutively but in any order.

18. The computer readable storage medium of claim 5, wherein the instructions also direct the at least one processor to:
store multiple copies of the pharmaceutical data that is modified by the first task and the second task, a first copy of the copies of the pharmaceutical data including the pharmaceutical data before execution of the first task, a second copy of the copies of the pharmaceutical data including the pharmaceutical data after execution of the first task, wherein the second task involves reviewing the pharmaceutical data that is changed; and display a first portion of the pharmaceutical data that is changed by the first task differently from a second portion of the pharmaceutical data that is not changed by the first task to at least one of the system requestors performing the second task.

19. The computer readable storage medium of claim 5, wherein the second task involves reverting the modification to the pharmaceutical data to restore the pharmaceutical data that was changed to a prior version of the pharmaceutical data.

20. The computer readable storage medium of claim 5, wherein the instructions also direct the at least one processor to:

restrict access to the pharmaceutical data by displaying only the subsets of the pharmaceutical data that are assigned to the system requestors.

\* \* \* \* \*

UNITED STATES PATENT AND TRADEMARK OFFICE
CERTIFICATE OF CORRECTION

PATENT NO. : 10,839,949 B1
APPLICATION NO. : 15/710793
DATED : November 17, 2020
INVENTOR(S) : David M. Hutchison et al.

Page 1 of 1

It is certified that error appears in the above-identified patent and that said Letters Patent is hereby corrected as shown below:

In the Claims

In Claim 8, Column 29, Line 49 delete "subsets"

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*